United States Patent
Hu

[19]

[11] Patent Number: 5,974,110
[45] Date of Patent: Oct. 26, 1999

[54] HELICAL RECONSTRUCTION ALGORITHM

[75] Inventor: Hui Hu, Waukesha, Wis.

[73] Assignee: General Electric Company, Milwaukee, Wis.

[21] Appl. No.: 08/979,101

[22] Filed: Nov. 26, 1997

[51] Int. Cl.[6] .................................................. A61B 6/03
[52] U.S. Cl. ................ 378/19; 378/15; 378/901
[58] Field of Search ...................... 378/4, 15, 19, 378/901

[56] References Cited

U.S. PATENT DOCUMENTS 5,541,970  7/1996  Hu ............................................. 378/4
5,559,847  9/1996  Hu et al. ..................................... 378/4

*Primary Examiner*—David Vernon Bruce
*Attorney, Agent, or Firm*—John S. Beulick; Christian G. Cabou; Phyllis Y. Price

[57] ABSTRACT

The present invention, in one form, is a method for performing image reconstruction from projection data acquired in a multislice helical scan. More specifically, helical weighting factors are generated and then applied to the collected data. The helical weighting algorithm provides a high quality image with a low level or number of artifacts is described. Such algorithm also reduces the total time required to reconstruct such an image.

10 Claims, 3 Drawing Sheets

HELICAL RECONSTRUCTION ALGORITHM

FIELD OF THE INVENTION

This invention relates generally to computed tomography (CT) imaging and more particularly, to the reconstruction of images from projection data acquired from a helical scan.

1. Background of the Invention

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the protection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. The projection data gathered with fan-beam helical scan can be denoted as $P(\theta,\gamma,z)$ where $\theta$ is the angle of the central ray of the fan beam with respect to some reference (e.g., the y axis), $\gamma$ is the angle of a particular ray within the fan beam with respect to the central ray, and z is the axial gantry position at the time the measurement is made.

For each location $z_0$ at which actual projection data is not obtained, a commonly used and known helical reconstruction algorithm produces raw data for a slice at location $z_0$ by using linear interpolation in the z direction. Specifically, to produce $P(\theta,\gamma,z_0)$, projection data at the same $\theta$ and $\gamma$ and as close as possible, but on opposite sides in z, to $z_0$ are used. For example, if $z_1$ and $z_2$ are the values of z for which $P(\theta,\gamma,z)$ are available, and for which $z_1 \leq z \leq z_2$, $P(\theta,\gamma,z_0)$ may be estimated from $P(\theta,\gamma,z_1)$ and $P(\theta,\gamma,z_2)$ by linear interpolation using the following:

$$P(\theta,\gamma,z_0) = \frac{z_2 - z_0}{z_2 - z_1} P(\theta,\gamma,z_1) + \frac{z_0 - z_1}{z_2 - z_1} P(\theta,\gamma,z_2). \quad (1)$$

In a helical scan, since the same ray is measured twice in each 360° rotation, i.e., $P(\theta,\gamma,z)=P(\theta+2\gamma+180°,-\gamma,z)$, the z sampling is effectively doubled. This increased sampling enables reducing the total scan time.

It is desirable, of course, to reconstruct images from the data obtained in a four beam helical scan in a manner which provides a high quality image with a low level or number of artifacts. It also is desirable to reduce the total time required to reconstruct such an image.

SUMMARY OF THE INVENTION

These and other objects may be attained in a system which, in one embodiment, generates projection space data arrays from projection data acquired by each fan beam in a four fan beam helical scan. Data in each array is then weighted by the system to correct for the translational motion of the patient and to offset data redundancy effects. An image is then reconstructed using the weighted data.

More specifically, in reconstructing an image, the system generates projection data arrays which correspond to data planes associated with the slice to be imaged. Weighting factors are then applied by the system to the data arrays to assign a weight to each particular data element. The weighted projection data arrays are then filtered and back projected to generate an image data array. The image data arrays are then summed to generate a slice image data array.

With respect to reconstructing a slice for a particular slice at a particular $z_0$ location at which projection data was not actually measured, and in one embodiment, the projection data for the z locations closest to, but on opposite sides of, the particular $z_0$ are identified. The projection data for the slice is then estimated using the projection data gathered at the identified z locations. The slice image can then be reconstructed using such estimated projection data.

The helical weighting factor for each data set, denoted as $W1(\beta,\gamma)$, $W2(\beta,\gamma)$, $W3(\beta,\gamma)$, and $W4(\beta,\gamma)$, respectively, are given as follows:

$$W1(\beta,\gamma) = W1(\beta) = \frac{1}{2} \begin{cases} 0 & \beta \leq \beta 3_- \\ \frac{\beta - \beta 3_-}{\beta 1 - \beta 3_-} & \beta 3_- < \beta \leq \beta 1 \\ \frac{\beta - \beta 2}{\beta 1 - \beta 2} & \beta 1 < \beta < \beta 2_- \\ 0 & \beta \geq \beta 2 \end{cases} \quad (2)$$

$$W2(\beta,\gamma) = W2(\beta) = \begin{cases} \frac{w2_1(\beta) + w2_2(\beta)}{2} & \beta \leq \beta 2 \\ \frac{\beta - \beta 3}{\beta 2 - \beta 3} & \beta 2 < \beta \leq \beta 3 \\ 0 & \beta \geq \beta 3 \end{cases} \quad (3)$$

where:

$$W2_1(\beta) = \begin{cases} 0 & \beta \leq \beta 1 \\ \frac{\beta - \beta 1}{\beta 2 - \beta 1} & \beta 1 < \beta \leq \beta 2 \end{cases}$$

$$W2_2(\beta) = \begin{cases} 0 & \beta \leq \beta 4_- \\ \frac{\beta - \beta 4_-}{\beta 2 - \beta 4_-} & \beta 4_- < \beta \leq \beta 2 \end{cases}$$

$$W3(\beta,\gamma) = W3(\beta) = \begin{cases} 0 & \beta \leq \beta 2 \\ \frac{\beta - \beta 2}{\beta 3 - \beta 2} & \beta 2 < \beta \leq \beta 3 \\ \frac{w3_1(\beta) + w3_2(\beta)}{2} & \beta > \beta 3 \end{cases} \quad (4)$$

-continued where:

$$W3_1(\beta) = \begin{cases} \dfrac{\beta - \beta 1_+}{\beta 3 - \beta 1_+} & \beta 3 < \beta < \beta 1_+ \\ 0 & \beta \geq \beta 1_+ \end{cases}$$

$$W3_2(\beta) = \begin{cases} \dfrac{\beta - \beta 4}{\beta 3 - \beta 4_-} & \beta 3 < \beta < \beta 4 \\ 0 & \beta \geq \beta 4 \end{cases}$$

$$W4(\beta, \gamma) = W4(\beta) = \dfrac{1}{2} \begin{cases} 0 & \beta \leq \beta 3 \\ \dfrac{\beta - \beta 3}{\beta 4 - \beta 3} & \beta 3 < \beta \leq \beta 4 \\ \dfrac{\beta - \beta 2_+}{\beta 4 - \beta 2_+} & \beta 4 < \beta < \beta 2_+ \\ 0 & \beta \geq \beta 2_+ \end{cases} \quad (5)$$

The weighting function described above is continuous. It is also independent of channel index, which provides a significant speedup gain.

With the above described weighting, the beam minimum full width at half maximum is 1.27 times the detector row collimation as measured at the axis of rotation. Thus, the present algorithm is not necessarily applicable for thin slice (1–1.2×) image reconstruction. However, in a thick slice mode (1.3–2×), the present algorithm is believed to provide high quality images at a very fast speed.

DETAILED DESCRIPTION

Figure 1:
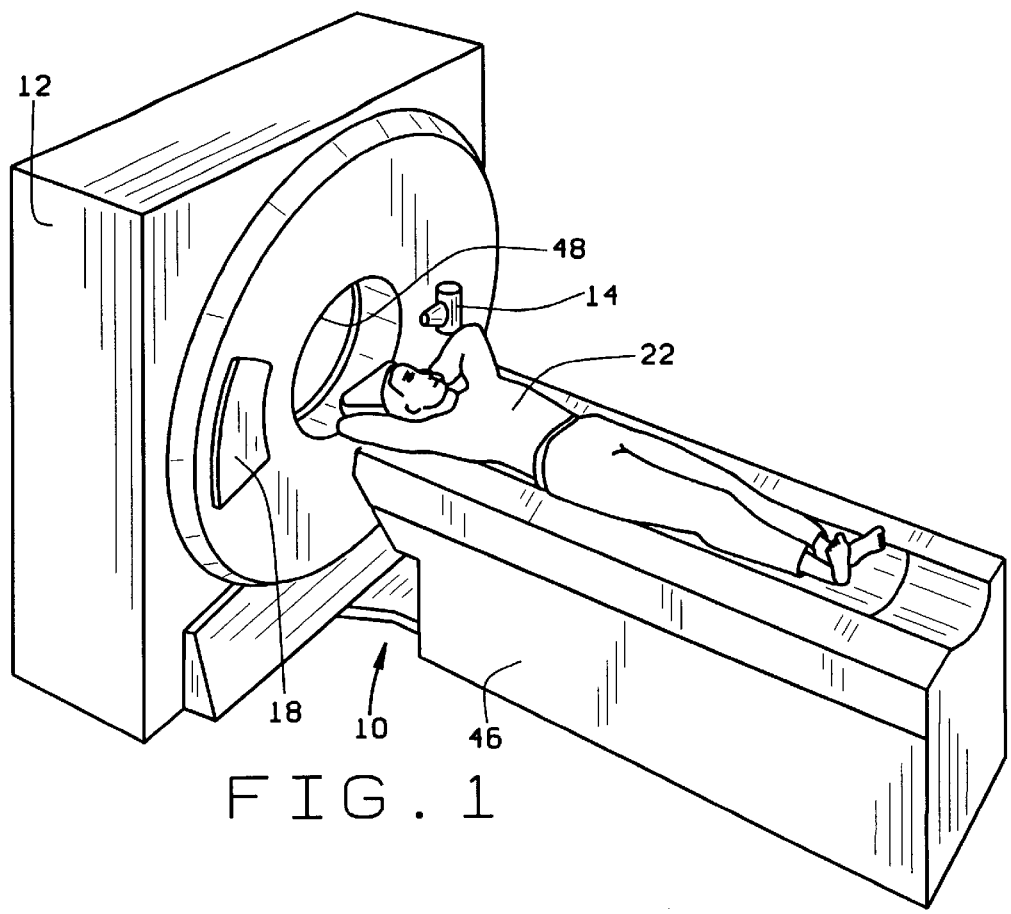
FIG. 1 is a pictorial view of a CT imaging system.
Figure 2:
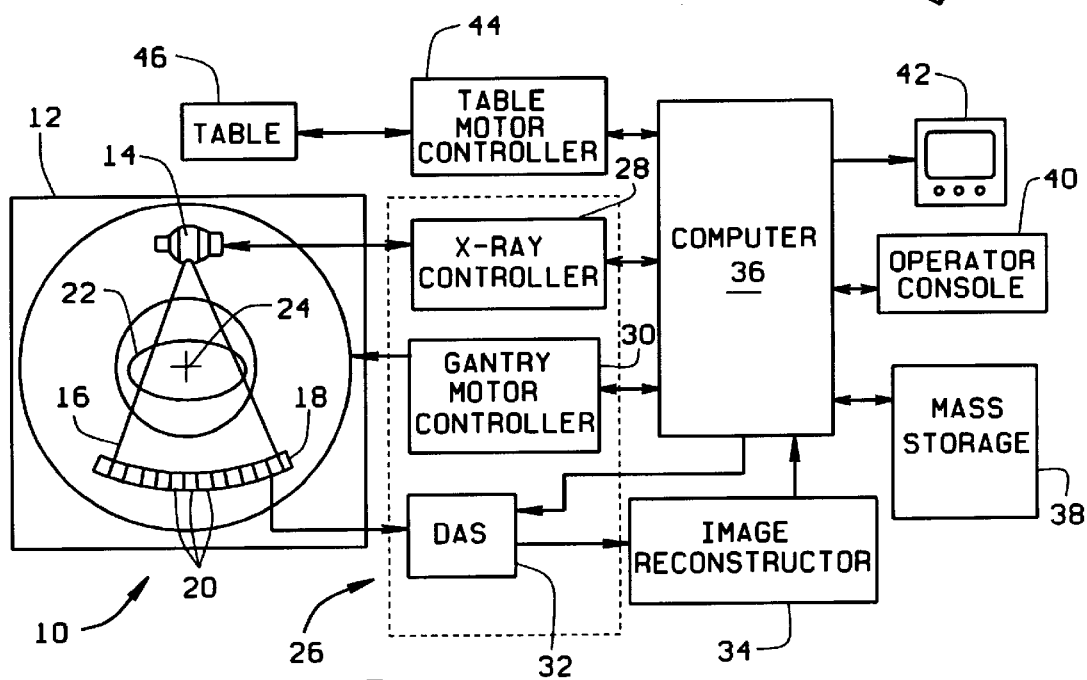
FIG. 2 is a block schematic diagram of the system illustrated in FIG.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about an axis of rotation 24.

Rotation of gantry 12 and the operation of x-ray source 14 are governed by a control mechanism 26 of CT system 10. Control mechanism 26 includes an x-ray controller 28 that provides powel and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion of a helical weighting algorithm sometimes refers specifically to multislice CT scanners, which typically include detector arrays have two to four rows of detector cells. The algorithm, however, is not limited to practice in connection with only two and four slice scanners and may be used with other CT scanners. Further, in one embodiment, the weighting algorithm would be implemented in computer 36 and would process, for example, data stored in mass storage 38. Many other alternative implementations are, of course, possible.

The simplified helical reconstruction algorithm described below is believed to be faster than known reconstruction algorithms without significant deterioration of image quality. In addition, the minimum image full width half maximum (FWHM) of the present algorithm is 1.27 times the detector row collimation as measured at the axis of rotation. Thus, the present algorithm is not necessarily applicable for thin slice (1–1.2×) image reconstruction. However, in a thick slice mode (1.3–2×), the present algorithm is believed to provide high quality images at a very fast speed.

The helical weighting described below could be used in connection with the systems, methods, and apparatus described in U.S. Pat. No. 5,559,847, which is assigned to the present assignee and hereby incorporated herein, in its entirety, by reference. More particularly, and in one embodiment, d denotes the spacing at the axis of rotation of fan beams defined by detector rows, s denotes the table feeding speed (per rotation), and p=d/s. For example, if the view angle is set to zero when the x-ray focal spot crosses the slice to be reconstructed, the angle at which each fan beam crosses the slice to be reconstructed at the axis of rotation is:

$$\beta 1 = -3p\pi \quad \beta 2 = -p\pi \quad \beta 3 = p\pi \quad \beta 4 = 3p\pi \quad (6)$$

Furthermore, $\beta_+$ and $\beta_-$ are defined as:

$$\beta 1+ = -3p\pi + 2\pi \quad \beta 3- = p\pi - 2\pi \quad (7)$$
$$\beta 2+ = -p\pi + 2\pi \quad \beta 4- = 3p\pi - 2\pi$$

Figure 3:
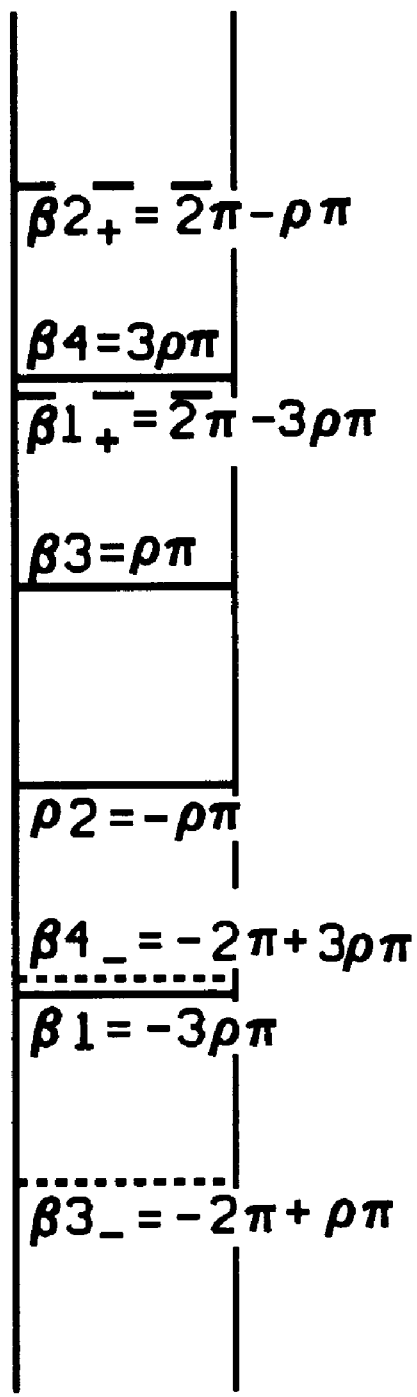
FIG. 3 is a sampling diagram illustrating data sampling a four row multislice detector.
Figure 4:
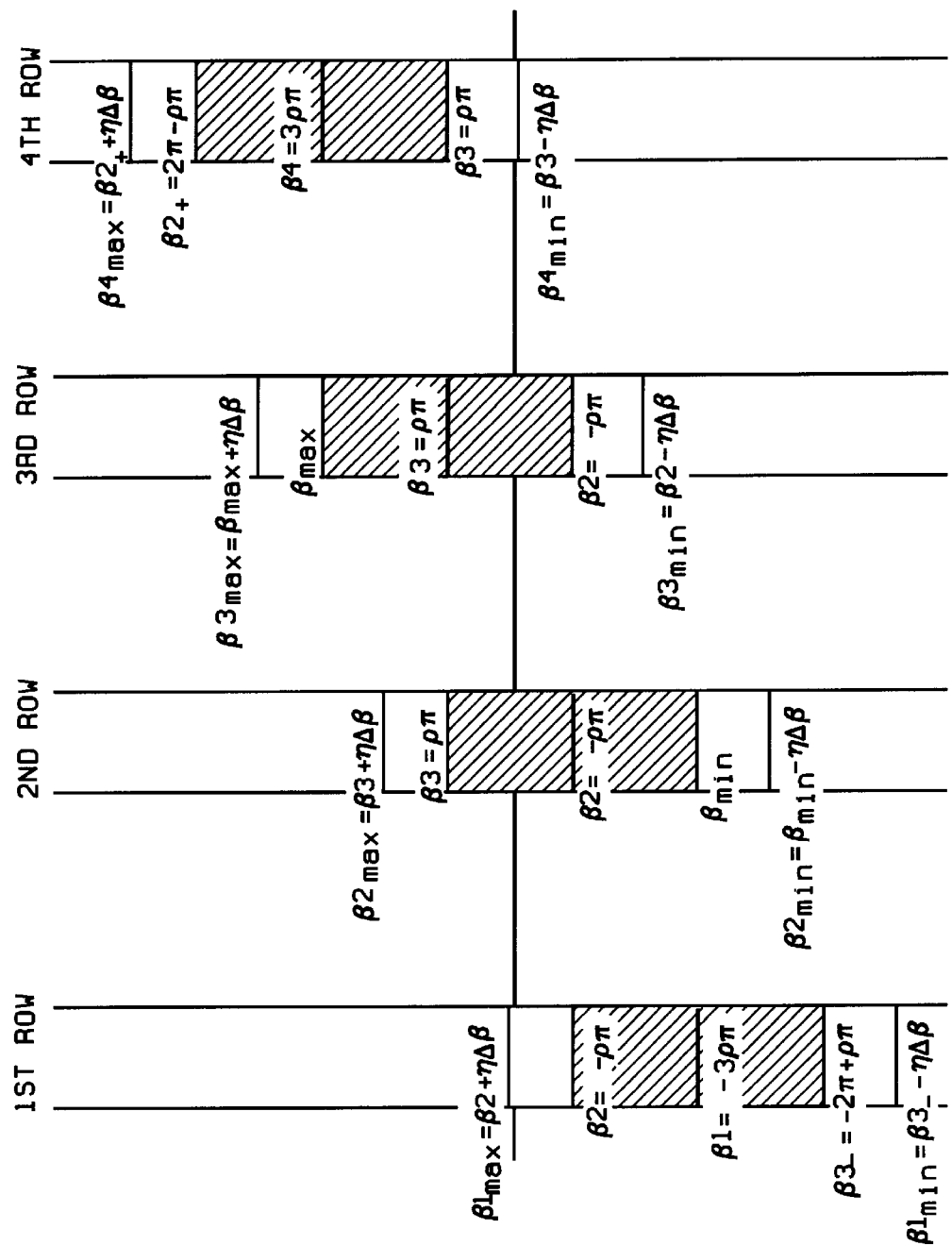
FIG. 4 illustrates weighting factors used in accordance with one embodiment of the present invention.

The relative positions of these angles are shown in FIGS. 3 and 4, where the $\beta_+$ and $\beta_-$ are denoted by dashed lines and dotted lines respectively.

With reference to FIGS. 3 and 4, the helical weighting factor for each data set, denoted as W1($\beta,\gamma$), W2($\beta,\gamma$), W3($\beta,\gamma$), and W4($\beta,\gamma$), respectively, are given as follows:

$$W1(\beta, \gamma) = W1(\beta) = \frac{1}{2} \begin{cases} 0 & \beta \leq \beta3_- \\ \frac{\beta - \beta3_-}{\beta1 - \beta3_-} & \beta3_- < \beta \leq \beta1 \\ \frac{\beta - \beta2}{\beta1 - \beta2} & \beta1 < \beta < \beta2_- \\ 0 & \beta \geq \beta2 \end{cases} \quad (8)$$

$$W2(\beta, \gamma) = W2(\beta) = \begin{cases} \frac{w2_1(\beta) + w2_2(\beta)}{2} & \beta \leq \beta2 \\ \frac{\beta - \beta3}{\beta2 - \beta3} & \beta2 < \beta \leq \beta3 \\ 0 & \beta \geq \beta3 \end{cases} \quad (9)$$

where:

$$W2_1(\beta) = \begin{cases} 0 & \beta \leq \beta1 \\ \frac{\beta - \beta1}{\beta2 - \beta1} & \beta1 < \beta \leq \beta2 \end{cases}$$

$$W2_2(\beta) = \begin{cases} 0 & \beta \leq \beta4_- \\ \frac{\beta - \beta4_-}{\beta2 - \beta4_-} & \beta4_- < \beta \leq \beta2 \end{cases}$$

$$W3(\beta, \gamma) = W3(\beta) = \begin{cases} 0 & \beta \leq \beta2 \\ \frac{\beta - \beta2}{\beta3 - \beta2} & \beta2 < \beta \leq \beta3 \\ \frac{w3_1(\beta) + w3_2(\beta)}{2} & \beta > \beta3 \end{cases} \quad (10)$$

where:

$$W3_1(\beta) = \begin{cases} \frac{\beta - \beta1_+}{\beta3 - \beta1_+} & \beta3 < \beta < \beta1_+ \\ 0 & \beta \geq \beta1_+ \end{cases}$$

$$W3_2(\beta) = \begin{cases} \frac{\beta - \beta4}{\beta3 - \beta4_-} & \beta3 < \beta < \beta4 \\ 0 & \beta \geq \beta4 \end{cases}$$

$$W4(\beta, \gamma) = W4(\beta) = \frac{1}{2} \begin{cases} 0 & \beta \leq \beta3 \\ \frac{\beta - \beta3}{\beta4 - \beta3} & \beta3 < \beta \leq \beta4 \\ \frac{\beta - \beta2_+}{\beta4 - \beta2_+} & \beta4 < \beta < \beta2_+ \\ 0 & \beta \geq \beta2_+ \end{cases} \quad (11)$$

The weighting function described above is continuous. It is also independent of channel index, which provides a speedup gain of hundred when compare with the original method.

The above described helical weighting algorithm provides a high quality image with a low level or number of artifacts is described. Such algorithm also reduces the total time required to reconstruct such an image.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

I claim:

1. A system for producing a tomographic image of an object from projection data acquired in a helical scan, said system including a four row detector array, said tomographic image system comprising an image reconstructor system configured to:

(a) create projection data arrays corresponding to the data obtained from each of the x-ray fan beams;

(b) apply a weighting function to each of the projection data arrays generated in step (a) to generate respective weighted projection data arrays, the weighting function to be applied for each data set, denoted as $W1(\beta,\gamma)$, $W2(\beta,\gamma)$, $W3(\beta,\gamma)$ and $W4(\beta,\gamma)$, being:

$$W1(\beta, \gamma) = W1(\beta) = \frac{1}{2} \begin{cases} 0 & \beta \leq \beta3_- \\ \frac{\beta - \beta3_-}{\beta1 - \beta3_-} & \beta3_- < \beta \leq \beta1 \\ \frac{\beta - \beta2}{\beta1 - \beta2} & \beta1 < \beta < \beta2_- \\ 0 & \beta \geq \beta2 \end{cases}$$

$$W2(\beta, \gamma) = W2(\beta) = \begin{cases} \frac{w2_1(\beta) + w2_2(\beta)}{2} & \beta \leq \beta2 \\ \frac{\beta - \beta3}{\beta2 - \beta3} & \beta2 < \beta \leq \beta3 \\ 0 & \beta \geq \beta3 \end{cases}$$

$$W2_1(\beta) = \begin{cases} 0 & \beta \leq \beta1 \\ \frac{\beta - \beta1}{\beta2 - \beta1} & \beta1 < \beta \leq \beta2 \end{cases}$$

$$W2_2(\beta) = \begin{cases} 0 & \beta \leq \beta4_- \\ \frac{\beta - \beta4_-}{\beta2 - \beta4_-} & \beta4_- < \beta \leq \beta2 \end{cases}$$

$$W3(\beta, \gamma) = W3(\beta) = \begin{cases} 0 & \beta \leq \beta2 \\ \frac{\beta - \beta2}{\beta3 - \beta2} & \beta2 < \beta \leq \beta3 \\ \frac{w3_1(\beta) + w3_2(\beta)}{2} & \beta > \beta3 \end{cases}$$

$$W3_1(\beta) = \begin{cases} \frac{\beta - \beta1_+}{\beta3 - \beta1_+} & \beta3 < \beta < \beta1_+ \\ 0 & \beta \geq \beta1_+ \end{cases}$$

$$W3_2(\beta) = \begin{cases} \frac{\beta - \beta4}{\beta3 - \beta4_-} & \beta3 < \beta < \beta4 \\ 0 & \beta \geq \beta4 \end{cases}$$

$$W4(\beta, \gamma) = W4(\beta) = \frac{1}{2} \begin{cases} 0 & \beta \leq \beta3 \\ \frac{\beta - \beta3}{\beta4 - \beta3} & \beta3 < \beta \leq \beta4 \\ \frac{\beta - \beta2_+}{\beta4 - \beta2_+} & \beta4 < \beta < \beta2_+ \\ 0 & \beta \geq \beta2_+ \end{cases}$$

2. A system in accordance with claim 1 wherein generating image data arrays comprises the step of performing filtration and back projection on each weighted projection data array.

3. A system in accordance with claim 2 wherein prior to performing filtration and back projection, data arrays from a same gantry angle but from different detector rows are combined.

4. A system in accordance with claim 3 wherein if a projection view in a first data row are three hundred and sixty degrees from the a projection view in a fourth data row, combining the views prior to filtration and back projection.

5. A system in accordance with claim 1 wherein prior to applying a weighting function to each of the projection data arrays, the data are stored in a system memory for reconstructing consecutive slices.

6. A method for producing a tomographic image of an object from projection data acquired from a four row detector array in a helical scan, said method comprising the steps of:

(a) creating projection data arrays corresponding to the data obtained from each of the x-ray fan beams;

(b) applying a weighting function to each of the projection data arrays generated in step (a) to generate respective weighted projection data arrays, the weighting factors to be applied for each data set, denoted as $W1(\beta,\gamma)$, $W2(\beta,\gamma)$, $W3(\beta,\gamma)$ and $W4(\beta,\gamma)$, being:

$$W1(\beta, \gamma) = W1(\beta) = \frac{1}{2} \begin{cases} 0 & \beta \leq \beta 3 \\ \frac{\beta - \beta 3_-}{\beta 1 - \beta 3_-} & \beta 3_- < \beta \leq \beta 1 \\ \frac{\beta - \beta 2}{\beta 1 - \beta 2} & \beta 1 < \beta < \beta 2 \\ 0 & \beta \geq \beta 2 \end{cases}$$

$$W2(\beta, \gamma) = W2(\beta) = \begin{cases} \frac{w2_1(\beta) + w2_2(\beta)}{2} & \beta \leq \beta 2 \\ \frac{\beta - \beta 3}{\beta 2 - \beta 3} & \beta 2 < \beta \leq \beta 3 \\ 0 & \beta \geq \beta 3 \end{cases}$$

$$W2_1(\beta) = \begin{cases} 0 & \beta \leq \beta 1 \\ \frac{\beta - \beta 1}{\beta 2 - \beta 1} & \beta 1 < \beta \leq \beta 2 \end{cases}$$

$$W2_2(\beta) = \begin{cases} 0 & \beta \leq \beta 4_- \\ \frac{\beta - \beta 4_-}{\beta 2 - \beta 4_-} & \beta 4_- < \beta \leq \beta 2 \end{cases}$$

$$W3(\beta, \gamma) = W3(\beta) = \begin{cases} 0 & \beta \leq \beta 2 \\ \frac{\beta - \beta 2}{\beta 3 - \beta 2} & \beta 2 < \beta \leq \beta 3 \\ \frac{w3_1(\beta) + w3_2(\beta)}{2} & \beta > \beta 3 \end{cases}$$

$$W3_1(\beta) = \begin{cases} \frac{\beta - \beta 1_+}{\beta 3 - \beta 1_+} & \beta 3 < \beta < \beta 1_+ \\ 0 & \beta \geq \beta 1_+ \end{cases}$$

$$W3_2(\beta) = \begin{cases} \frac{\beta - \beta 4}{\beta 3 - \beta 4_-} & \beta 3 < \beta < \beta 4 \\ 0 & \beta \geq \beta 4 \end{cases}$$

$$W4(\beta, \gamma) = W4(\beta) = \frac{1}{2} \begin{cases} 0 & \beta \leq \beta 3 \\ \frac{\beta - \beta 3_-}{\beta 4 - \beta 3} & \beta 3 < \beta \leq \beta 4 \\ \frac{\beta - \beta 2_+}{\beta 4 - \beta 2_+} & \beta 4 < \beta < \beta 2_+ \\ 0 & \beta \geq \beta 2_+ \end{cases}$$

7. A method with claim 6 wherein generating image data arrays comprises the step of performing filtration and back projection on each weighted projection data array.

8. A method in accordance with claim 7 wherein prior to performing filtration and back projection, and the data arrays from a same gantry angle but from different detector rows are combined.

9. A method in accordance with claim 8 wherein if a projection view in a first data row are three hundred and sixty degrees from the a projection view in a fourth data row, combining the view prior to performing filtration and back projection.

10. A method in accordance with claim 7 wherein prior to applying a weighting function to each of the projection data arrays, storing the data in a system memory for reconstructing consecutive slices.

* * * * *